(12) United States Patent
Cadwalader et al.

(10) Patent No.: US 8,840,052 B1
(45) Date of Patent: Sep. 23, 2014

(54) CONTAINMENT AND PRODUCT EXTRACTION OF GRAIN ENDOSPERM

(76) Inventors: Robert E. Cadwalader, Glen Elyn, IL (US); Rex A. Dieterle, Madison, WI (US)

( * ) Notice: Subject to any disclaimer, the term of this patent is extended or adjusted under 35 U.S.C. 154(b) by 440 days.

(21) Appl. No.: 13/373,686

(22) Filed: Nov. 25, 2011

(51) Int. Cl.
*B02C 9/00* (2006.01)

(52) U.S. Cl.
USPC ...... 241/9; 241/12; 241/20; 241/21; 426/481; 426/518

(58) Field of Classification Search
USPC .................. 426/481, 518; 241/21, 24.1, 6–13
See application file for complete search history.

(56) References Cited

U.S. PATENT DOCUMENTS 5,250,313 A 10/1993 Giguere
7,524,522 B2 4/2009 DeLine et al.

OTHER PUBLICATIONS

Xu W, Reddy N, Yang Y, "An acidic method of zein extraction from DDGS;" *J Agric Food Chem.*, Jul. 25, 2007; 55(15): 6279-84.
Chein-Shyong Su, "A novel method for continuous production of cyclodextrins using an immobilized enzyme system;" *Journal of Chemical Technology and Biotechnology*, vol. 48, Issue 3, pp. 313-323, 1990.
Tae-Jong Kim, "Production of cyclodextrin using raw corn starch without a pretreatment;" *Enzyme and Microbial Technology*;vol. 20, Issue 7, pp. 506-509, May 1997.
Biwer, G. Antranikian and E. Heinzle, "Enzymatic production of cyclodextrins;" *Applied Microbiology and Biotechnology*, vol. 59, No. 6, pp. 609-617, 2002.

*Primary Examiner* — Mark Rosenbaum
(74) *Attorney, Agent, or Firm* — Tipton L. Randall

(57) ABSTRACT

A process for converting, separating and removing conversion products from grain endosperm using a contained reaction vessel to effect conversions and extractions. The process minimizes particulate interference with equipment, thereby lowering operating and capital expense. Successive conversion and extraction processes reuse major system parts in each step. The process steps comprise: (a) charging the containment vessel with grain endosperm; (b) inputting extraction fluids (liquids or gases) to the system; (c) circulating extraction fluids through the contained endosperm at conducive temperatures, pressures, contact times and flow rates to effect extraction; (d) removing extraction fluids containing the products from the system; (e) optionally, input flush fluids to the system to further remove remaining products; (f) optionally, blowing down the system with gasses, further removing remaining products; (g) continuing conversion and extraction of remaining grain endosperm to remove further products; (h) finally, removing remaining grain endosperm solids.

22 Claims, 7 Drawing Sheets

CONTAINMENT AND PRODUCT EXTRACTION OF GRAIN ENDOSPERM

CROSS-REFERENCE TO RELATED APPLICATIONS, IF ANY

Not applicable.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates to an economical and technically available suite of processes for the processing of corn and other grain endosperms in a contained manner to make successive conversions and extractions of useful products for further processing or as end products without the transfer of the endosperm out of the container and extraction system. The ultimate goal of the conversions and extractions is to minimize or eliminate any residual endosperm out of the process container and lower or eliminate interfering particulates from the products for further processing or end use and sale.

Using endosperm only grain products eliminate processing problems involving the fats, oils, proteins and hull particulate matter which cause process problems in the conversion and extraction of desired products of the endosperm and further process problems of the conversion products.

The use of the invention will result in higher value products from the endosperm material and cost savings in the conversions and further processing of the conversion products.

2. Background Information

The processing of grains, particularly corn, to alternate fuel products such as acetone, butanol and, particularly, ethanol is becoming of major importance to the US and world economy. More than 30% of the corn produced in the US goes to ethanol production, and the amount shows a steady increase from 0% 30 years ago. Grains are also becoming an important source of alternate feedstock chemicals to either replace high-priced oil-based products, such as zein plastics and cylodextrins in industrial, food and pharmacological uses, or because of their unique biodegradable and biologically safe (GRAS) nature.

There is, however, a complication over the use of grain products to produce alternate fuels or other chemical products. The commodity prices for the grains are subject to international pressures of rising populations and affluence. This has driven grain prices up and requires new levels of efficiency in processing the grains. A major example of this put 40 of the about 150 dry grind corn ethanol plants into bankruptcy in 2008 when the price of corn rose above the selling price of their two major products, ethanol and the co-product the remaining corn residue called distiller dry grains (DDGS) for animal feed. A similar economic problem existed in 2011 where the corn commodity price for corn and other grains outpaced any rise in fuel ethanol prices.

Some of the corn ethanol producers attempted to broaden their revenue sources by attempting to recover oils and other components downstream of the fermentation and distillation process. Unfortunately, because the whole corn kernel is ground up prior to sugar conversion, fermentation and distillation, the conditions (high temperature/pressure, chemicals) used in the upstream conversion steps can adversely affect the quality and quantity of oils, proteins and other desired components, as well as making the additional product recovery methods inefficient and expensive.

Now several dry milling technologies have become available from companies such as POET, ICM, Inc, MOR Technology LLC and Cereal Process Technology LLC to separate the oil and high quality protein containing germ, as well as the outer hull or bran from the grain kernel in a low energy dry milling process. (DeLine, U.S. Pat. No. 7,524,522; Giguere, U.S. Pat. No. 5,250,313) High quality oil can be recovered from the germ, while the endosperm fraction (starch/protein) continues on through the ethanol production process, making highly efficient use of processing equipment. Only one known major corn ethanol plant is using this dry milling process (instead of the dry grind process). However, because of the general poor economics of the corn/grain ethanol plant investment, and the improved return on investment (ROI) seen by using the dry grind process, the major co-products, except the recovered germ, remain low cost animal feed products comparable to distillers dry grains.

The natural extension to using the Dry Mill process is to pre-process the endosperm and extract clean fermentation sugars for the ethanol process, processing to acetone, butanol and ethanol or other high value alternate energy products. Since the remaining endosperm is still contained within the extraction system, additional high value chemicals contained in the endosperm are easily recovered, such as endosperm proteins and, particularly, the zein proteins. Additional conversion operations are performed on the remaining endosperm to match the range of corn-based chemicals produced in the wet mill corn industry.

The present invention permits the production of high value products from the grain endosperm. These materials can be the primary product, as well as a high value product secondary to the grain-based starch to sugar fermentation product. An example is the production of high value cylodextrins as a secondary product, during the conversion of the endosperm starch to dextrins, oligosaccharides and sugars for subsequent fermentation to energy products. A high value cylodextrin co-product is produced and all the remaining endosperm is converted to fermentation products and high value protein products, removing all need for waste treatment processes associated with a single process cylodextrin production facility.

SUMMARY OF THE INVENTION

The invention is a process for containment and product extraction of grain endosperm comprising the steps; (a) providing a system including a vessel having a contained volume therein for retaining grain endosperm and allowing passage of extraction fluids through the contained volume; (b) depositing grain endosperm within the contained volume; (c) passing a plurality of extraction fluids sequentially through the grain endosperm within the contained volume to extract selected components therefrom and sequentially remove each extraction fluid with selected components therein from the system; and (d) removing grain endosperm residual, if any, from the contained volume and from the system.

In a further embodiment of the invention, two or more endosperm containment vessels are provided within the system to permit continuous or semi-continuous operation of the process.

The invention also includes a process for containment and product extraction of grain endosperm comprising the steps; (a) providing a system including a vessel having a contained volume therein for retaining a ground grain endosperm and allowing passage of fluids through the contained volume; (b) depositing a ground grain endosperm having particles sized between 0.5 mm and 20 mm within the contained volume; (c) passing a first aqueous liquid phase containing enzymes through the ground grain endosperm within the contained volume at a selected temperature, pressure and pH for a time sufficient to produce dextrins, oligosaccharides, and sugars soluble in the aqueous liquid phase, then removing the first aqueous liquid phase from the system; (d) passing first a gas, then a second aqueous liquid phase, then another gas through the contained volume to remove residual first aqueous liquid phase from the ground grain endosperm and from the system; (e) passing an aqueous alcohol liquid phase through the ground grain endosperm within the contained volume at a selected temperature, pressure and pH to extract zein proteins therefrom, then removing the aqueous alcohol liquid phase containing the zein proteins from the system; (f) passing first a gas, then a third aqueous liquid phase through the contained volume to remove residual aqueous alcohol liquid phase from the ground grain endosperm and from the system; and (g) passing a fourth aqueous liquid phase containing a strong acid through the ground grain endosperm within the contained volume at a selected temperature and pressure for a time sufficient to dissolve remaining ground grain endosperm and produce nutrient material soluble in the fourth aqueous liquid phase, then removing the fourth aqueous liquid phase containing the nutrient material from the system.

In further embodiments of the invention, the aqueous liquid phase containing multiple components is concentrated and fractionated by filtration to produce separate aqueous solutions containing selected soluble components.

DESCRIPTION OF THE EMBODIMENTS

The invention is a method of converting, separating and removing various conversion products from grain endosperm using a contained reaction vessel to effect the conversions and extractions. The method minimizes particulate interference with the process equipment, thereby lowering the operating and capital expense of the overall processes. The unique aspect of the contained extraction method is making successive conversion and extraction processes convenient by reuse of the major parts of the system in each step of the process.

The method comprising the steps of (a) charging the endosperm containment vessel with the grain endosperm; (b) inputting the extraction fluids (be they in the liquid or gaseous form) to the system; (c) circulating the extraction fluids through the contained endosperm at conducive temperatures, pressures, contact times and flow rates to make the extraction; (d) removing the extraction fluids with the products from the system; (e) optionally, inputting flush fluids to the system to further remove any remaining products; (f) optionally, blowing down the system with air or other gasses to further remove any remaining products; (g) continuing the conversion and extraction process on the remaining grain endosperm to remove further products; and (h) if necessary, removing any remaining grain endosperm in solid form.

Figure 1:
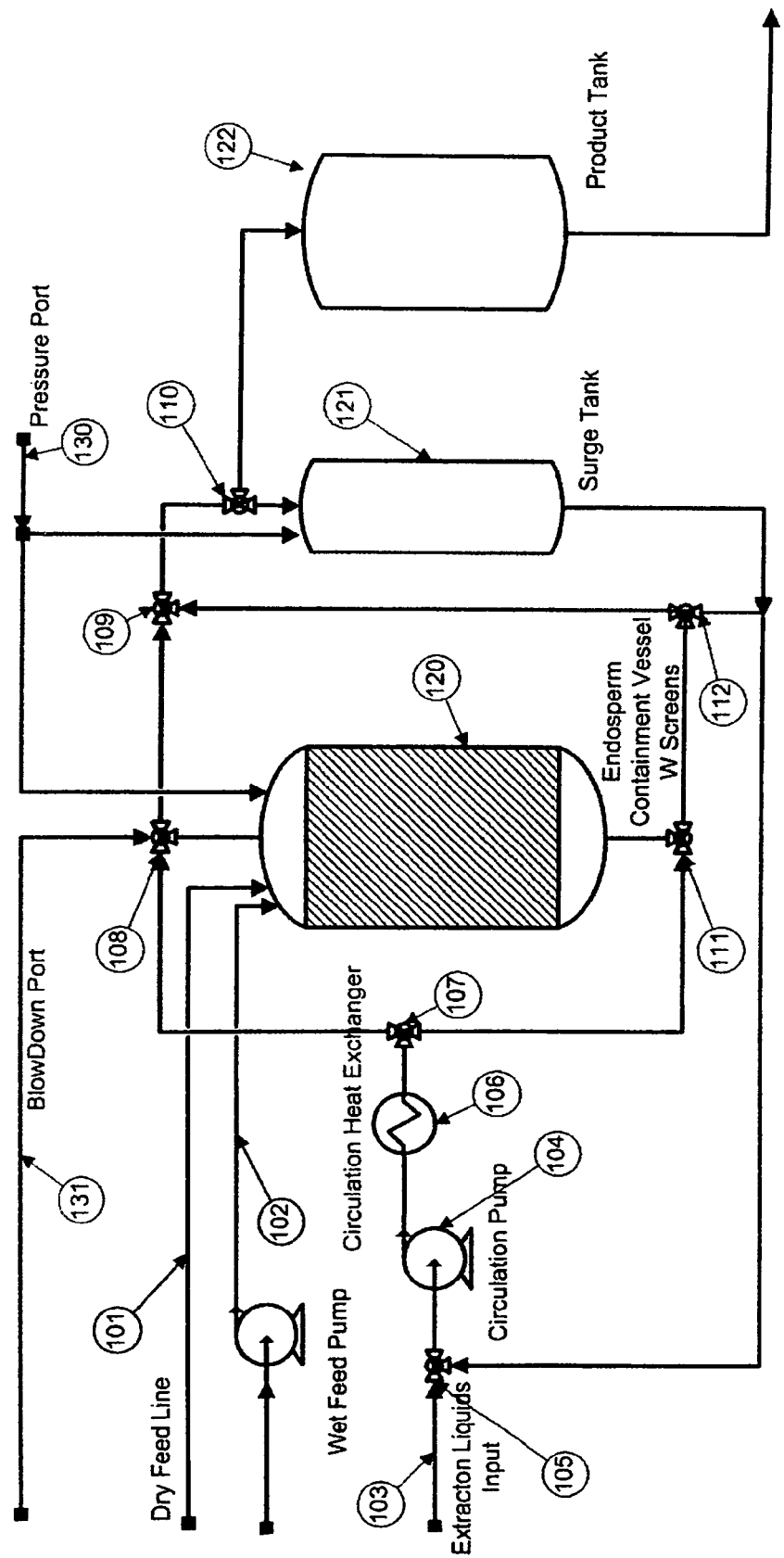
FIG. 1 is a schematic illustration of the basic invention configuration to charge, convert and remove products from the contained grain endosperm.

The following is an overview of the process. The examples further illustrate how the basic invention is used in various forms, without limiting the scope of the present invention. FIG. 1 illustrates one embodiment of the basic system of the present invention. The endosperm containment vessel (120) is charged with a specified amount of grain endosperm that is either whole or ground to a specified size distribution, depending on the extraction process recipe. Again, depending on the process recipe, the endosperm is charged either in dry form (101) or as slurry (102). The endosperm containment vessel (120) may take several forms in the containment of the endosperm particles with screening methods internal to containment vessel dependent on the operation of the conversion and extraction process selected. FIG. 3A-3F illustrates alternative containment configurations for the endosperm, to be described later.

A measured amount of extraction fluid enters the system, via line (103), into the circulation pump (104), and through the recirculation valve (105), although this valve is optional. This fluid contains extraction chemicals such as acids, bases, enzymes, organisms, hydrocarbons etc., usually with an additional carrier fluid, such as water, alcohols, hydrocarbon fluids etc. The extraction fluid flows directly to the circulation surge tank (121) through the heat exchanger (106) to condition the temperature of the fluid by adding or removing heat and then, through valves (107), (108), (109) and (110). The extraction fluid is circulated without going through the endosperm containment vessel until proper temperature conditioning of the extraction fluid is achieved. System pressure is regulated through system pressure line (130). Alternately, the extraction fluid makes a first pass through the endosperm containment vessel (120) through valves (108) for top feed or valve (111) for bottom feed, and then flows to the surge tank (121).

With the initial charge of conversion and extraction fluid complete, the fluid is then circulated through the endosperm containment vessel until the conversion and extraction reaction conditions are met. This can be as short as one pass of the total fluid through the endosperm medium, or more commonly, from minutes to hours for the conversion and extraction reaction.

When the conversion and extraction process is completed, the fluid is routed out of the system to a product tank (122), then out of the system to some other activity or storage vessel. A typical end of process method is to recondition the fluid by either lowering or raising the temperature and/or pressure to stop any reactions. This makes the fluid more conducive to storage or secondary reactions, which is accomplished by cycling the fluid through both the surge tank (122) and the endosperm containment vessel (120), or bypassing the endosperm containment vessel (120) and only including the surge tank (121).

Once the extraction fluid is conditioned, the surge tank is drained by moving fluid through the circulation pump (104) and then out of the system through a valve (110). The endosperm containment vessel (120) is simultaneously drained in the process, using the bottom evacuation valve (112). It is recommended that the system then be gas evacuated, or "blown down," to further remove any remaining fluid contained in the endosperm matrix, and to remove any fluids remaining in the system piping. The blow down port and line (131) is activated, and a gas enters the system under sufficient pressure to remove remaining fluids from the system. The gases can be filtered air or other processed gases, such as nitrogen, carbon dioxide, etc.

Optionally, a flush of the system can be performed. The flush fluid enters the system in place of the extraction fluids (103) and follows a similar path through the system, through the circulation pump (104), and is conditioned through the heat exchanger (106). The flush fluid optionally goes through the surge tank (121), through a valve (110), or it is confined to the endosperm containment vessel (120) only through valves (107), (108), (111) and (112). The flush fluid is then evacuated from the system through the valve (110) and out of the system. In some cases, the flush fluid is routed to the surge tank (121), which functions as a storage vessel, instead of leaving the system. This option is employed if the flush fluid is used in a subsequent reaction on the endosperm. Generally, after the fluid flush, the whole system is "blown down" again following the steps outlined above.

When the initial endosperm conversion and extraction reaction has been completed and the system "blown down" and flushed, the system is now ready for one or more subsequent conversion and extraction reactions. Because the remaining solid endosperm is still contained in the endosperm containment vessel, and only liquids and very fine particulates have left the system, the endosperm is in an ideal condition for further fluid extraction.

Figure 2:
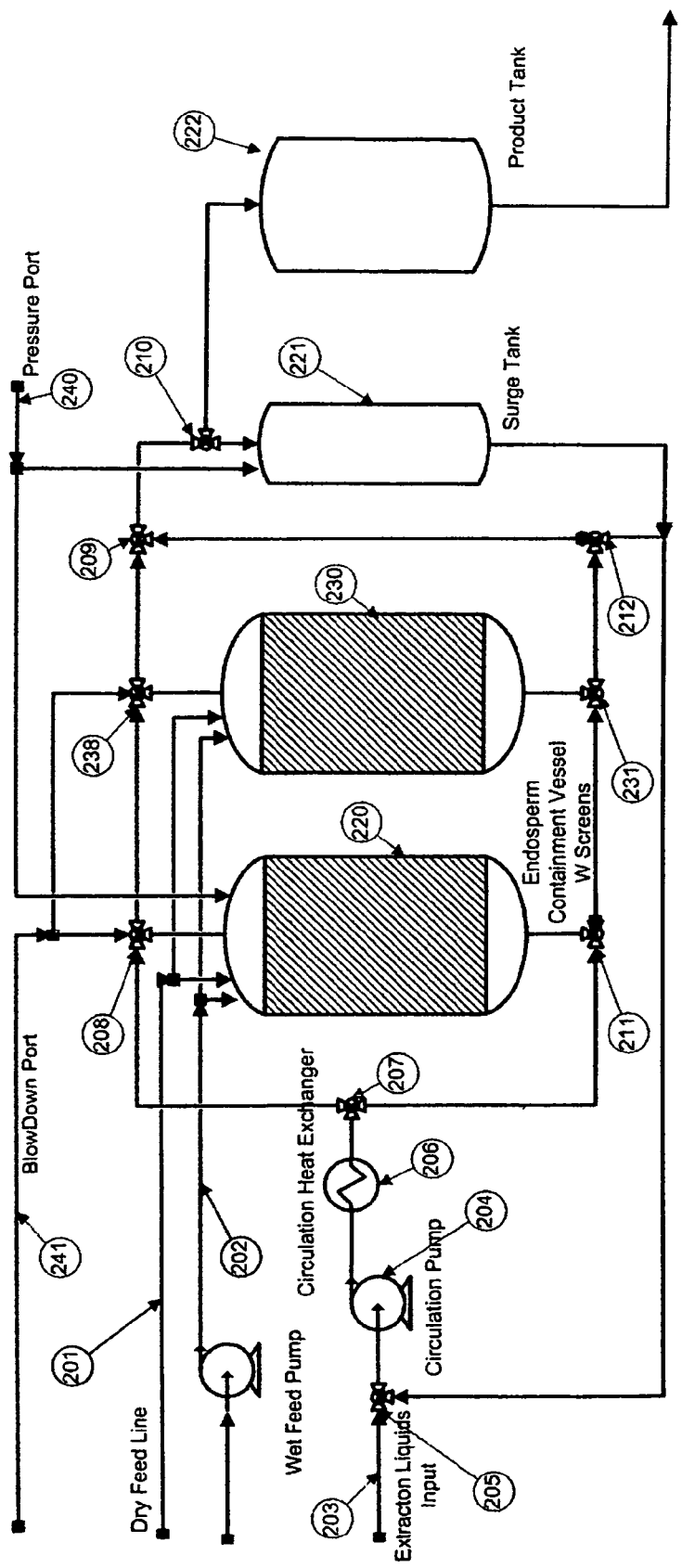
FIG. 2 is a schematic illustration of the basic invention configuration illustrating another configuration of multiple endosperm containment vessels in a bank-switching mode.

FIG. 2 demonstrates an extension of the basic system design, where two or more endosperm containment vessels are included in the basic process system to permit continuous or semi-continuous operation of the system. The "bank switching" of the containment vessels permits charging certain static reaction processes, and discharging one vessel, while the other vessel is in a different phase of a series of conversion and extraction operations. In this system configuration, two or more endosperm containment vessels operate in parallel, with the remaining system components configured, as in FIG. 1. Thus, operation of two or more containment vessels in parallel enables performance of nonidentical process steps in a single time period for the two or more containment vessels, and continuous or semi-continuous operation of the whole system.

There is also a significant array of physical internal configurations of the endosperm containment vessel to accomplish the extraction process. FIG. 3A-3F illustrates various internal arrangements, described in detail below.

Figure 3A:
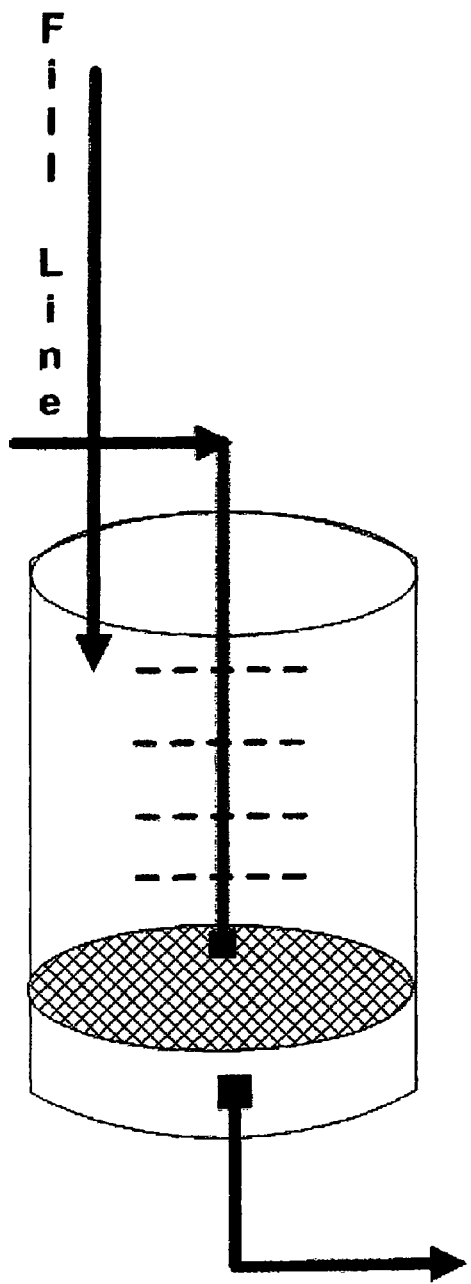
FIG. 3A is a schematic illustration of one embodiment of the containment configuration within the containment vessel of the present invention.

FIG. 3A illustrates a bottom filter arrangement. The endosperm is charged into the vessel from the top, either as a dry solid or as a suspended fluid slurry. The fluid enters the top of the vessel either directly or through a system of spargers, flowing up through the endosperm media, and exiting the vessel at the bottom for recycle. Fine particulates that initially leave the containment vessel are recycled back through the containment vessel and screen for subsequent conversion and entrapment.

Figure 3B:
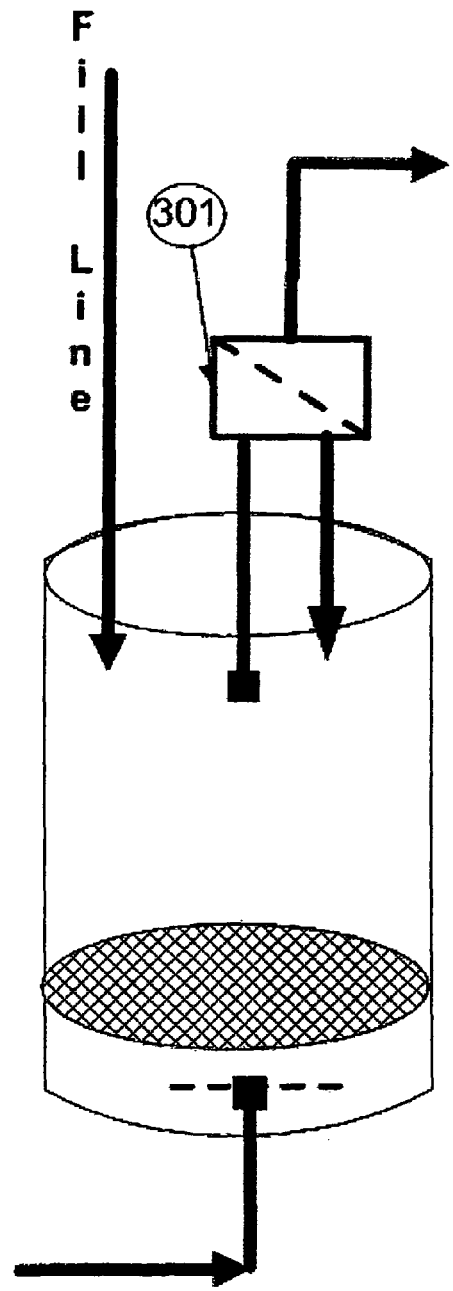
FIG. 3B is a schematic illustration of another embodiment of the containment configuration within the containment vessel of the present invention.

FIG. 3B illustrates a bottom filter arrangement. The endosperm is charged into the vessel from the top either as a dry solid or as a suspended fluid slurry. The fluid enters the bottom of the vessel either directly or through a system of spargers, flowing up through the endosperm media, and exits the vessel at the top for recycle. The flow velocity distribution, preferably, is laminar flow and is low enough to prevent physical movement of the endosperm particles. Alternatively, the flow velocity distribution is sufficiently high to suspend the particles, as in a fluidized bed arrangement, for improved fluid/solid contact. Optionally, the vessel system contains a secondary fines filter (310), configured to collect and recycle any fine endosperm particles back into the containment vessel for further processing.

Figure 3C:
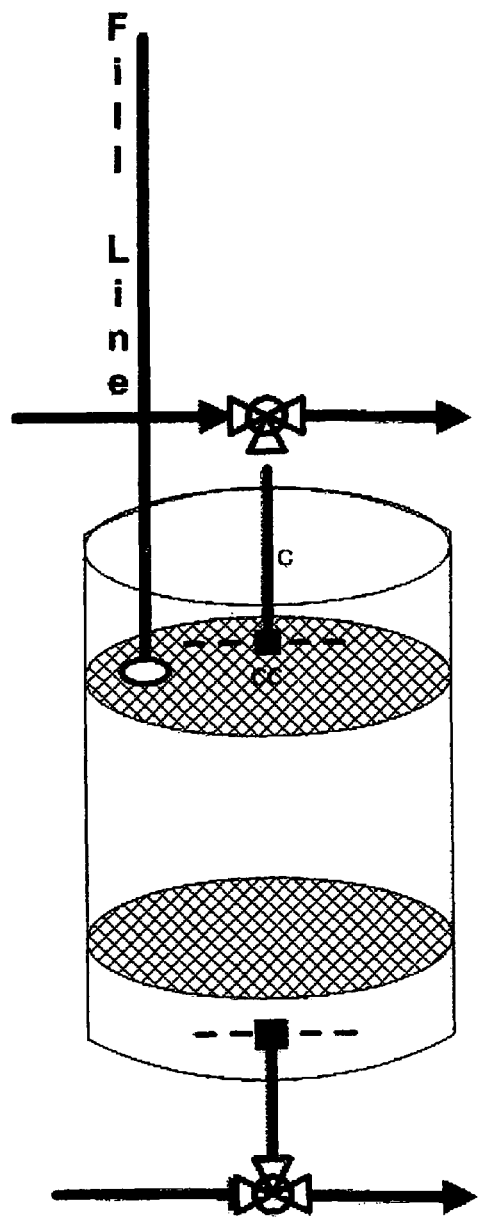
FIG. 3C is a schematic illustration of yet another embodiment of the containment configuration within the containment vessel of the present invention.

FIG. 3C illustrates a bottom or top feed vessel with screens at the top and bottom of the vessel. The endosperm is charged into the vessel from the top, either as a dry solid or as a suspended fluid slurry, through a port in the top or bottom screen. As in FIG. 3A, the fluid enters the vessel from the bottom directly or through a sparger system and flows up though the system with the endosperm participles contained in the system by the top filter. Conversely, the system can be configured to have the fluid enter from the top of the vessel directly or through a sparger system and flow down through the endosperm and leave the vessel from the bottom for recycle. The initial charge of the endosperm is deposited into the vessel through a port in the top screen (shown) or the bottom screen (not shown).

Figure 3D:
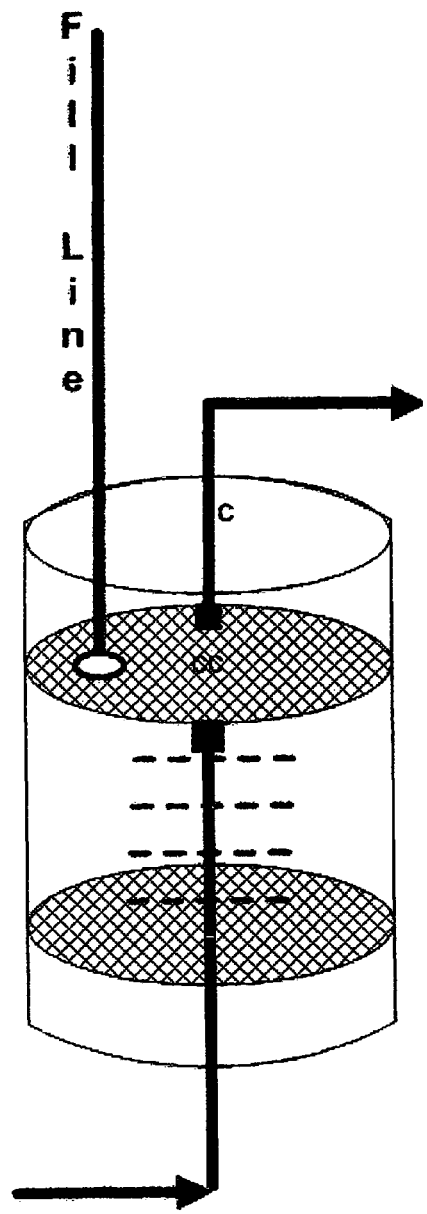
FIG. 3D is a schematic illustration of yet another embodiment of the containment configuration within the containment vessel of the present invention.

FIG. 3D illustrates a bottom feed configuration with the fluid entering the endosperm at multiple points through a system of spargers. This configuration permits more complex forms of fluid distribution into the endosperm, and encourages local turbulent flow, when necessary. The fluid exits the system though the top screen. The endosperm is charged into the vessel from the top, either as a thy solid or as a suspended fluid slurry, through a port in the top screen (shown) or the bottom screen (not shown).

Figure 3E:
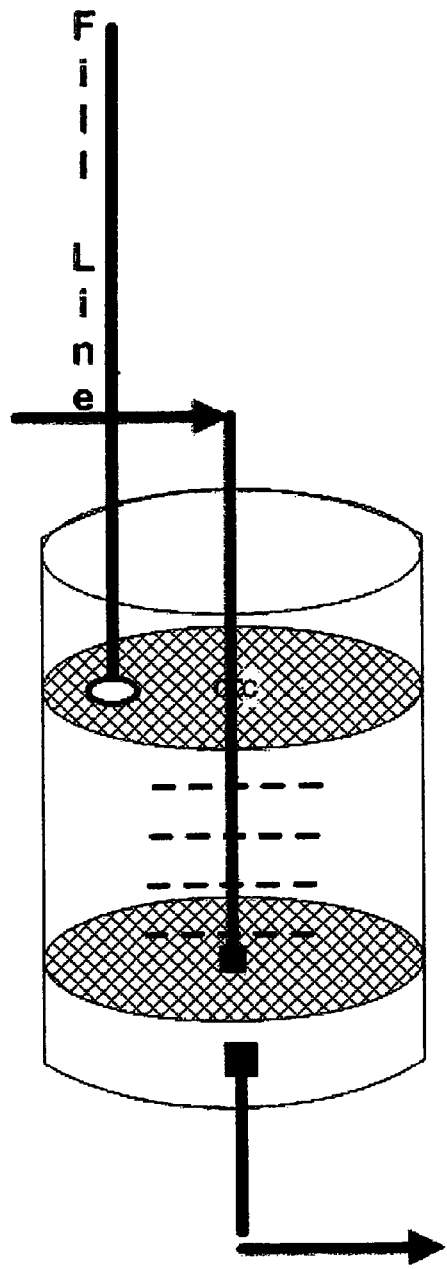
FIG. 3E is a schematic illustration of yet another embodiment of the containment configuration within the containment vessel of the present invention.

FIG. 3E shows a similar distributed fluid flow as in FIG. 3D, but with the feed from the top of the vessel and the exit at the vessel bottom. The endosperm is charged into the vessel from the top either as a dry solid or as a suspended fluid slurry, through a port in the top screen (shown) or the bottom screen (not shown).

Figure 3F:
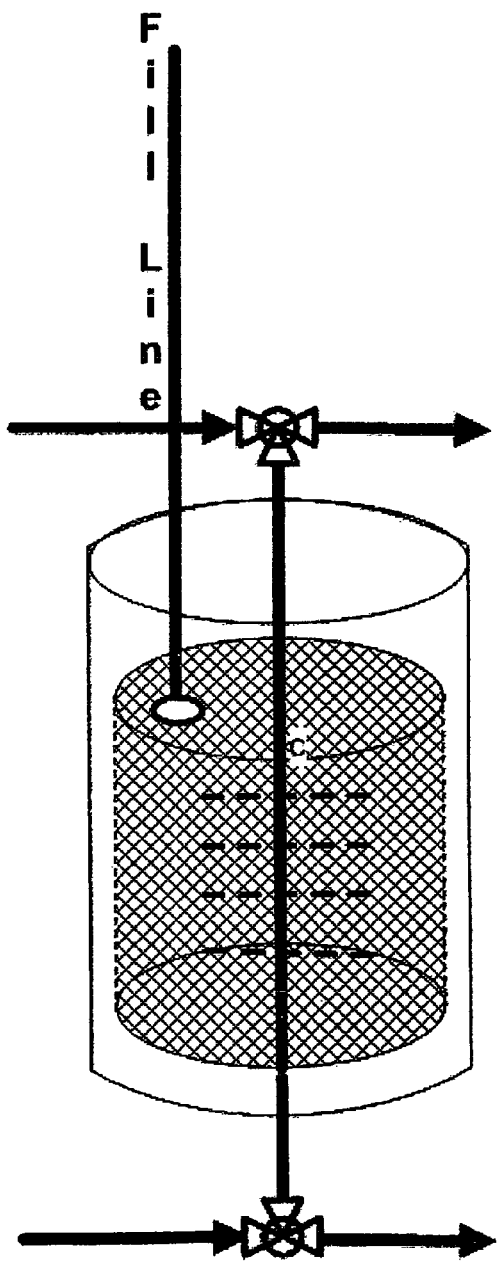
FIG. 3F is a schematic illustration of yet another embodiment of the containment configuration within the containment vessel of the present invention.

FIG. 3F illustrates a screen basket as the containment method. This configuration permits further turbulent contact, with the fluid exiting the containment basket in all directions. Preferably, a sparger for fluid entry internal to the basket is part of the system. Overall fluid flow is from the bottom to the top of the vessel, or in an overall top to bottom flow. The endosperm is charged into the vessel from the top either as a dry solid or as a suspended fluid slurry, through a port in the top screen (shown) or the bottom screen (not shown).

EXAMPLES

Example 1

This is an example of a 100 million gallon a year (MGY) corn ethanol plants conversion of corn endosperm starch to a 30% by weight concentration of sugars for fermentation to ethanol, the subsequent extraction of zein proteins, and finally, conversion of the remaining solids to a protein rich nutrient supplement suitable for addition to the fermentation process.

In this example, one or more 50,000 gallon containment vessels, such as illustrated in FIGS. 3A to 3F, are used, although other vessel configurations are contemplated. The overall system configuration is that shown in FIG. 1. The bottom, top and side screen opening size is between 4 mm to 8 mm. The vessel is dry filled with a charge of 190,000 lbs of endosperm per vessel. The particle size grind is from a screen opening range of 0.5 mm to 20 mm. Depending on the nature of the corn type used and endosperm configuration of hard or soft, the largest particle size possible produces the best results. The passing screen particle size used in this example is 10 mm. The nominal dry density of the ground endosperm charge is about 40 to 45 lbs/cubic foot, depending on grind size. The vessel is charged to 67% of its working volume to allow for swelling of the endosperm on hydration. Final dry weight density of the hydrated endosperm is 25 to 35 lbs/cubic foot, depending on grind size. Vessel volume also allows for flotation expansion of the endosperm during processing.

The first process entails the conversion of the endosperm starch with alpha-amylase enzymes. The extraction liquid is water of high quality, such as filtered water, water processed by ultra filtration or reverse osmosis or similar processes, which contains starch conversion enzymes of the alpha-amylases type and optionally additionally enzymes of the glucoamylase type. Optionally, the extraction liquid is the flush fluid from a previous starch conversion processes, as described here, and contains low levels of dextrins, oligosaccharides and sugars. An extraction fluid charge of 40,000 to 50,000 gallons of suitably purified water of high quality is added. The extraction fluid contains 0.5 gm to 2 gm per pound of starch of alpha-amylase and 0.1 gm to 2.5 gm per pound of starch of glucoamalase. The volume of enzyme addition depends on the activity and operating conditions of the enzymes used and the level of residual starch conversion products contained in the flush fluid from a previous starch conversion operation, when used as the extraction fluid charge.

There is a broad field of alpha-amylases available from the starch conversion industry using moderate operating temperature from 80° F. to high operating temperature of 230° F. and solution pH from 2.5 to 6.5. Heat is added or removed from the system through a heat exchanger 106, shown in FIG. 1, and the temperature is controlled by the heat exchanger as the fluid circulates through the containment vessel.

The typical hydrated corn endosperm has a pH of 5.5 to 6.0. Thus, pH adjustment may be necessary, depending on the range of operating pH of the enzyme configuration selected. However, pH adjustment generally is not necessary with the selection of starch conversion enzymes operating in the natural hydrated endosperm pH range.

The low molecular weight dextrins and oligosaccharides produced are then concurrently converted to fermentable sugars, either totally or partially, during the process by glucoamylase enzymes. The glucoamylase enzymes are added in the initial extraction liquid charge. Once the process temperature and pH are reached, typical process time is from 0.5 hours to 8 hours, depending on the enzymes chosen, the enzyme dose level, process temperature chosen, fluid velocities through the containment vessel and the level of conversions targeted. Full conversion of starch to dextrins and oligosaccharides is preferred in order to remove all the starch from the endosperm for further processing. However, complete conversion to fermentable sugars is not desirable if very high gravity (VHG) fermentation to ethanol is selected for subsequent conversion of the fluid from this part of the process.

Suitable alpha amalyses and glucoamalyses are available from Genencor, Novozyme, Sygenta, Verenium, WeissBioTech or similar manufactures.

Upon the completion of the process of converting the endosperm starches to dextrins, oligosaccharides and sugars, the conversion fluids are removed from the system with the circulation pump and other pumps, if necessary, to the fermentation holding tank and then to the ethanol fermentation operation.

Residual dextrins, oligosaccharides and sugars are left in the converted endosperm, as well as small amounts of the conversion enzymes. These components are recovered by a gas "blow down" with filtered air, filtered nitrogen, filtered $CO_2$ or similar non-reactive gasses to remove most of the remaining fluid clinging to the processed endosperm. The second process is flushing the remaining endosperm with water of high quality, pretreated as outlined above. The flushing extraction fluid is circulated several times through the endosperm to remove the remaining dextrins, oligosaccharides and sugars. A second gas "blow down" with filtered air, filtered nitrogen, filtered $CO_2$ or similar non-reactive gasses is then performed. A second flush is usually necessary to fully remove the remaining dextrins, oligosaccharides and sugars. The second flush is followed by a third gas "blow down" with filtered air, filtered nitrogen, filtered $CO_2$ or similar non reactive gasses to remove most of the remaining fluid clinging to the processed endosperm.

The total volume of the flush extraction fluid is calculated to match the volume of extraction fluid water necessary to process a second batch of endosperm to the required sugar concentration for fermentation. The flush fluid is stored for use as extraction fluid for subsequent batches of endosperm and, hence, no sugars or residual enzymes are lost from the total operation.

The next operation on the remaining endosperm extracts zein proteins therefrom. Dry endosperm is generally 85% to 90% convertible starch and 7% to 9% protein with the remaining material fiber and ash. With the starch removed, the remaining endosperm contains 60% to 80% protein. Zein protein content of the remaining protein is 40% to 70%, depending on the type of corn processed. The dry weight of the remaining endosperm is greatly reduced over the starch laden starting endosperm. However, the wet volume is 30% to 60% of the starting endosperm volume since the remaining endosperm is hydrated in the range of 60% to 90% water.

The zein proteins are extracted by circulating at 70% (v/v) ethanol-water mixture at a temperature of 50° F. to 160° F. (optimum at 70° F.). About 5,000 to 6,000 gallons of dehydrated ethanol per vessel from the fuel ethanol process is fed into the system, depending on the moisture level of the residual endosperm. The process temperature is adjusted by the circulation heat exchanger. The fluid is circulated for a period of 0.5 to 5 hours (optimum of 1 hour) until the zein protein is extracted into the ethanol/water fluid.

At the end of the zein protein extraction process the process fluid is pumped out of the system. The endosperm containment vessel and total circulation system then undergoes a gas "blow down" with filtered air, filtered nitrogen, filtered $CO_2$ or similar non reactive gas, to remove most of the remaining fluid clinging to the processed endosperm. The "blow down" is followed by addition of a small amount of purified water, one-tenth to two tenths of the process volume, to flush the system of any remaining ethanol liquid or vapor. The zein protein containing fluids are further processed in other processes to concentrate and/or precipitate the zein protein in the extraction fluid. The ethanol and water in the process fluid is then flashed to purify the ethanol water solution, and then dehydrated in the fuel ethanol distillation and drying process.

The third and final process on the remaining endosperm in this example is the digestion of the remaining unrecovered zein protein and other proteins, as well as remaining endosperm carbohydrate and other materials. At least 40% to 70% of the zein proteins are removed in process step 2 and the remaining endosperm is 5% to 8% of its starting dry weight. This remaining material is digested primarily to liquefy it and convert the remaining proteins to nitrogen compounds easily incorporated as nutrients in the ethanol fermentation process.

A process fluid of 2,000 to 10,000 gallons per vessel of a 1% to 5% sulfuric, nitric or similar strong acid solution is circulated through the remaining endosperm in the containment vessel. The digestion temperature is between 190° F. to 250° F., and the pressure is between 0.6 atmospheres to 2.0 atmospheres. The temperature and resulting pressures are controlled by the recirculation heat exchanger and pressure controls on the containment vessel. The process time is between 0.5 and 4 hours for the digestion processes.

After digestion, the temperature and pressure of the fluids in the system are lowered to the range of 70° F. to 120° F. or a similar convenient handling and storage temperature. The remaining liquified endosperm is then removed from the system to storage from the fermentation process. The system is then flushed with a process volume 5% of the system volume, about 2,500 gallons per vessel, of high purity water or another convenient volume to purge and clean the system for subsequent use.

Example 2

Figure 4:
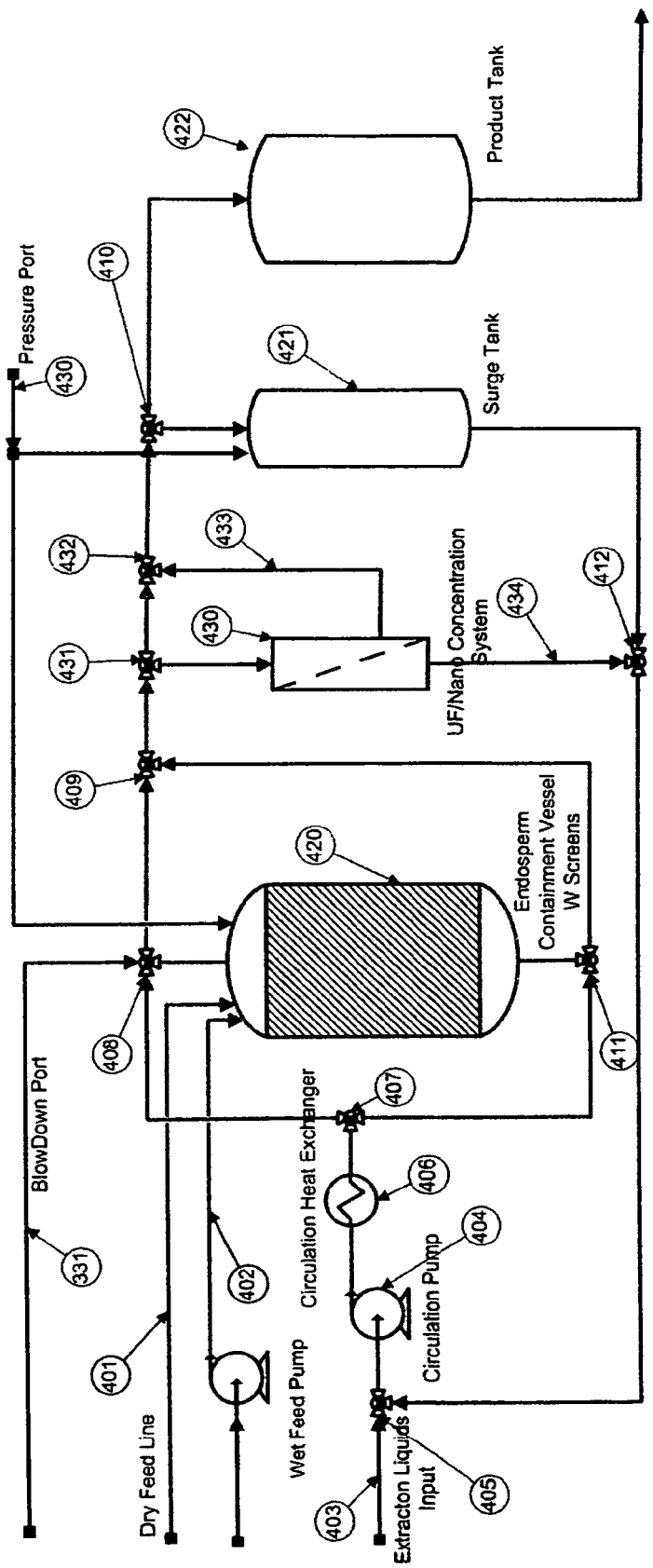
FIG. 4 is a schematic illustration of a further embodiment of the basic design to charge, convert and remove products from the system utilizing a ultra-filtration and reverse osmosis system to further concentrate products continuously from the product conversion and extraction loop of the present invention.

This is an example of 25 million gallons a year (MGY) corn ethanol plants conversion of corn endosperm starch to a particulate free, high concentration dextrins, oligosaccharides and sugars solution, suitable for continuous fermentation through a low sugar concentration circulation loop and continuous concentration with an ultrafiltration or a nanofiltration system (UF/NANO system). FIG. 4 illustrates this modification of the basic system. The low concentration loop fluid containing the conversion enzymes plus other components, is retained for subsequent endosperm starch conversions, thereby significantly reducing enzyme costs and reducing the amount of flush water to remove retained dextrins, oligosaccharides and sugars in the remaining endosperm matrix.

As in Example 1, the remaining endosperm goes through a zein protein extraction. The remaining endosperm solids are digested and removed from the system to be incorporated into the corn bran from the endosperm separation process used as high protein animal feed material.

In this example, one or more 9,000 gallon containment vessels illustrated in FIGS. 3A to 3F, or a similar configuration are used. The bottom screen opening size is between 4 mm to 8 mm. The vessel is dry or wet filled with a charge of 35,000 lbs of endosperm per vessel. The particle size grind is from a screen opening range of 0.5 mm to 20 mm. Depending on the nature of the corn type used and endosperm configuration of hard or soft, the largest particle size possible produces the best results. The passing screen particle size of this example is 10 mm. The nominal dry density of the ground endosperm charge is about 40 to 45 lbs/cubic foot depending on grind size. The vessel is charged to 67% of its working volume to allow for swelling of the endosperm on hydration. Final dry weight density of the hydrated endosperm is 25 to 35 lbs/cubic foot, depending on grind size. Vessel volume also allows for flotation expansion of the endosperm during processing.

The first process entails the conversion of the endosperm starch conversion with alpha-amylase enzymes. The extraction liquid is water of high quality, such as filtered water, water processed by ultra filtration or reverse osmosis, or similar processes, which contains starch conversion enzymes of the alpha-amylases type and, optionally, additionally enzymes of the glucoamylase type. The extraction liquid is the 5% to 15% concentration conversion and extraction fluid, plus the flush fluid from a previous starch conversion processes, as described below. The conversion and extraction recirculation loop is set at from 5% to 15% concentration of dextrins, oligosaccharides and sugars or a similar low concentration by the addition of 25,000 to 100,000 gallons of high quality water described above, or fluid from the previous dextrins, oligosaccharides and sugars extraction process.

As in Example 1, the process temperature and pH are similar, depending on the enzymes and enzyme concentration chosen. The enzyme charge is 5% to 50% of the enzyme charge in Example 1, since all the enzymes are retained in the extraction fluid from the previous endosperm extraction process. The refreshing enzyme charge amount depends on the specific activity loss of the enzyme, based upon the operating conditions selected as to pH, temperature and reaction time. Because of the lower concentration of dextrins, oligosaccharides and sugars in the extraction circulation loop, the conversion is more efficient, and process times are reduced by 10% to 40%.

The fluid is circulated through the endosperm containment vessel, as in Example 1, and is then routed to an ultrafiltration or a nanofiltration (UF/NANO) system (430) through valves (409) and (431). The UF/NANO system consists of an industrial standard series and parallel arrangement of ultrafiltration or nanofiltration membranes with internal feed and recirculation pumps, plus other internals. The system produces an unfiltered recycle fluid, a concentrated fluid and a permeate fluid with a reduced concentration of dextrins, oligosaccharides and sugars, which is routed back to the circulation loop.

The ultrafiltration system (UF) continuously concentrates the process fluid of dextrins, oligosaccharides and sugars to a concentration higher then the recirculation fluid, and continually removes the concentrated fluid (433) from the system. The concentrated fluid is a 30% to 45% concentration of dextrins, oligosaccharides and sugars. All the enzymes in the process are retained in the conversion and extraction loop and are recycled back to the conversion fluid as a more dilute fluid retaining the unconverted starch and intermediate products, as well as the conversion enzymes, (434) through a valve (412).

Alternatively, the nanofiltration system (NANO) also continuously concentrates the process fluid of dextrins, oligosaccharides and sugars to a sugar concentration higher then the recirculation fluid, and continually removes the concentrated fluid (433) from the system. The concentrated fluid is a 30% to 45% concentration essentially of sugars. All the enzymes, dextrins and oligosaccharides in the process are retained in the conversion and extraction loop and are recycled back to the conversion fluid as a more dilute fluid retaining the unconverted starch and intermediate products, as well as the conversion enzymes, (434) through a valve (412).

The removed fluid volume is made up by adding high quality water to the system through the input line (403) and the valve (405) to maintain the dextrins, oligosaccharides and sugars concentration at constant levels. Later in the process, as the starch is depleted and the products are removed, high quality water is added to the fluid circulation system to keep the circulation fluid volume constant.

Upon the completion of the process of converting the endosperm starches to dextrins, oligosaccharides and sugars, the conversion fluids are removed from the system with the circulation pump and other pumps, if necessary, to the fermentation hold tank and then to the ethanol fermentation operation.

Residual dextrins, oligosaccharides and sugars are left in the converted endosperm, as well as small amounts of the conversion enzymes. These are recovered, first by a gas "blow down" of the containment vessel with a gas and then flushing the remaining endosperm with water of high quality, as outlined previously, and then by a second "blow down" with a gas, as in Example 1. A second water flush is usually not required.

The total volume of the flush extraction liquid is calculated to match the volume of extraction fluid water necessary to process a second batch of endosperm to the required sugar concentration for fermentation. The flush fluid is stored for future use as extraction fluid for subsequent batches of endosperm and, hence, no sugars or residual enzymes are lost from the total operation.

The next operation on the remaining endosperm extracts zein proteins from the remaining endosperm. The zein proteins are extracted using an acidic ethanol extraction incorporating a reducing agent, as described by Xu W, Reddy N, Yang Y, "An acidic method of zein extraction from DDGS;" *J Agric Food Chem.*, 2007, Jul. 25; 55(15): 6279-84.

Between 900 to 1200 gallons of dehydrated ethanol per vessel from the fuel ethanol process are fed into the system, depending on the moisture level of the residual endosperm, to produce a 70% (v/v) ethanol-water mixture. An additional 600 to 1500 gallons of 70% (v/v) ethanol-water mixture are added to the system per vessel to bring the solvent to solids ratio to between 8% and 10%. The circulating extraction fluid is then adjusted to a pH of 1 to 2 with hydrochloric acid or a similar strong acid. The fluid pH is held between pH 1 and 2 with the addition of more acid or the addition of a base, such as sodium hydroxide. Next, 70 to 90 pounds of a reducing agent, such as sodium sulfite, sodium bisulfite, cysteine or similar material, are added to the extraction fluid, providing a reducing agent concentration of 0.2% to 0.025% by weight in the extraction fluid. The extraction fluid is then heated to 140° F. to 175° F. Upon reaching the operating temperature, the extraction fluid is circulated through the residual endosperm for 20 minutes to 40 minutes.

At the end of the zein protein extraction process, the process fluid is pumped out of the system. The endosperm containment vessel and total circulation system then proceeds to a gas "blow down" with filtered air, filtered nitrogen, filtered $CO_2$ or similar non reactive gasses to remove most of the remaining fluid clinging to the processed endosperm. The "blow down" is followed by adding a small amount of purified water, one-tenth to two tenths of the process volume, to flush the system of any remaining ethanol liquids of vapors. The zein protein containing fluids are further processed to concentrate and/or precipitate the zein protein in the extraction fluid. The ethanol and water in the process fluid is then flashed to purify the ethanol water solution and then dehydrated in the fuel ethanol distillation and drying process.

The remaining endosperm is then digested to a low solids liquid, as in Example 1, then neutralized to a pH 6 to pH 7 and removed from the system. This material is mixed with the bran fraction from the dry mill process to produce a high fiber, high protein animal feed product.

Example 3

This is an example of the conversion of grain endosperm starch to cylodextrins and a particulate free high concentration dextrins, oligosaccharides and sugars solution, suitable for continuous fermentation. Cylodextrins are a high value product that sells for $10 to $400 per pound, compared to ethanol at $0.30 to $0.45 per pound. These materials are produced commercially by direct conversions of grain starch, but are also obtained in low quantities, through secondary conversions in the corn ethanol fermentation process. Cylodextrins are produced from starch, dextrins, and oligosaccharides by the enzyme cyclodextrin glycosyltransferase, which is closely related to alpha-amylase. Processes to convert starch, dextrins, and oligosaccharides can use cyclodextrin glycosyltransferase, singly or in combination with alpha-amalyses and glucoamalyses. Such processes are described by Chem-Shyong Su, "A novel method for continuous production of cyclodextrins using an immobilized enzyme system;" *Journal of Chemical Technology and Biotechnology*, Vol. 48, Issue 3, pp. 313-323, 1990; Tae-Jong Kim, "Production of cyclodextrin using raw corn starch without a pretreatment;" *Enzyme and Microbial Technology*; Vol. 20, Issue 7, pp. 506-509, May, 1997; and Biwer, G. Antranikian and E. Heinzle, "Enzymatic production of cyclodextrins;" *Applied Microbiology and Biotechnology*, Volume 59, No. 6, pp. 609-617, 2002.

Figure 5:
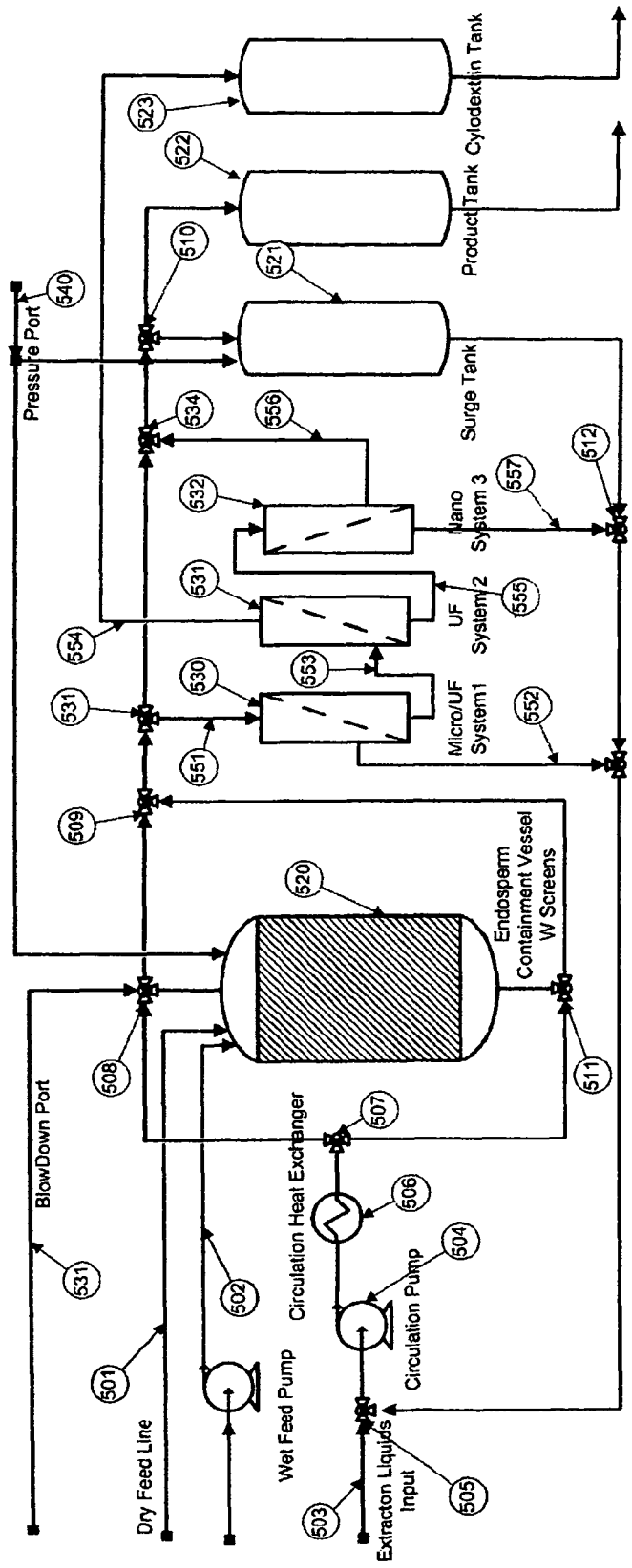
FIG. 5 is a schematic illustration of a further embodiment of the basic design to charge, convert and remove multiple products from the system utilizing multiple membrane systems to remove products continuously from the product conversion and extraction loop of the present invention.

Using the contained endosperm process, cylodextrins are produced in commercial quantities during the starch, dextrins, oligosaccharides conversion process of Example 2. The cylodextrins produced are continually separated from the conversion and extraction fluid as they are produced through a membrane system, as shown in FIG. 5. Unconverted materials are recycled back to the conversion process, as well as all the conversion enzymes and non-cylodextrin conversion products. The cylodextrins are continually removed from the system, and the fermentable dextrins, oligosaccharides and sugars are then concentrated and removed from the conversion system continually, and sent to a fermentation process. Depending on the design and economics of the process, between 1% and 50% of the starch is converted to cylodextrins. As in Examples 1 and 2, the non-starch remaining endosperm fraction is processed to remove the zein proteins, and then the remaining proteins and other endosperm material are liquified and removed from the system for other uses.

As in Examples 1 and 2, the vessel is charged as either a wet charge or dry charge through lines 501 or 502 to about 67% of its working volume to allow for swelling of the endosperm on hydration. Vessel volume is also allowed for flotation expansion of the endosperm during processing.

The first process step entails endosperm starch conversion to cylodextrins, as well as other dextrins, oligosaccharides and sugars with cyclodextrin glycosyltransferase enzymes, alone or in combination with alpha-amylase enzymes and glucoamylase enzymes. Cyclodextrin glycosyltransferase enzymes have a broad range of operating conditions very similar to alpha-amylases enzymes. Typical cyclodextrin glycosyltransferase enzymes, suitable for the process, are available from Genencor, Novozyme, Sygenta, Verenium, Weiss-BioTech or similar manufactures.

The extraction liquid is water of high quality, such as filtered water, water processed by ultra filtration, reverse osmosis or similar processes. The water contains starch conversion enzymes of the alpha-amylases type and optionally, additionally enzymes of the glucoamylase type. The extraction fluid loop is set at a 5% to 15% concentration of dissolved solids by the membrane systems operating parameters concentration and the addition of high quality water, described above, or fluid from the previous cylodextrin, dextrins, oligosaccharides and sugars production and extraction process.

The enzyme concentrations of the process fluid is set at 0.5 to 2.0 grams per pound of starch of active cyclodextrin glycosyltransferase enzymes and 0.2 to 1.0 grams per pound of starch of active alpha-amylase and 0.1 to 2.5 grams per pound of starch of active glucoamalase. The volume of enzyme addition depends on the activity and operating conditions of the enzymes used and the level of residual starch conversion products contained in the flush fluid from a previous starch conversion operation.

As all enzymes are of the amylases family, moderate operating temperature from 80° F. to 230° F. and solution pH from 2.5 to 8.5 are suitable. The optimal temperature range is 140° F. to 180° F. for the conversion with a pH range of 4 to 7. The typical hydrated corn endosperm has a pH of 5.5 to 6.0. Thus, pH adjustment with the addition of an acid or base may be necessary, depending on the operating pH of the enzyme configuration selected. However, pH adjustment generally is not necessary when the selected starch conversion enzymes operate in the natural hydrated endosperm pH range. Heat is added or removed from the system through the heat exchanger (506) and the temperature controlled by the heat exchanger as the fluid circulates through the containment vessel.

The conversion and extraction fluids and make up fluid (503) enters the system and circulates continually through the endosperm containment vessel. The temperature of the fluid is adjusted to the operating temperature by the heat exchanger (506). The pH, enzyme concentration and operating concentration are adjusted by the addition of enzymes, acids or bases, and make up fluid, all added through the extraction fluid input line (503) and the valve (505).

The extraction fluid circulates through the endosperm containment vessel (520), as in Example 2, and the fluid (551) is then routed to the first of three membrane separation systems, a micro/UF system 1 (530), a series/parallel arrangement of microfiltration membranes and ultra-filtration membranes, through the valves (509) and (531). The solids and high molecular weight partially digested liquid starch (552) is retained by micro/UF system 1 (530) and recycled back to the main conversion and extraction fluid loop. The filtration system 1 (530) passes the conversion products, the cylodextrins, dextrins, oligosaccharides and sugars, in the stream (553) to a second membrane filtration system (531) for separation of the cylodextrins from the dextrins, oligosaccharides and sugars.

Ultrafiltration system 2 (531) is a series/parallel arrangement of ultra-filtration membranes, which retains and concentrates the larger cylodextrin molecules and passes the smaller molecular weight dextrins, oligosaccharides and sugars. A concentrated stream of cylodextrins (554) is continually removed from the ultra-filtration membrane system and directed to a storage tank (523). The dextrins, oligosaccharides and sugar stream (555) is routed to the third membrane system (532) for concentration.

The nanofiltration system 3 (532) is a series/parallel arrangement of nanofiltration membranes, which concentrate the small molecular weight dextrins, oligosaccharides and sugars. The retentate is continually removed from the nanofiltration system through the stream (556) and directed through the valves (534) and (510) to the product tank, as in Examples 1 and 2, for fermentation. The dilute permeate of the membrane system (557), as in Example 2, is routed back to the primary circulation loop for reprocessing. The amount of fluid removed from the system is made up by continually adding water of high quality to the circulation fluid loop through the input port (503) and the valve (505).

Residual cylodextrins, dextrins, oligosaccharides and sugars remain in the converted endosperm, as well as small amounts of the conversion enzymes. These materials are recovered by a gas "blow down" with filtered air, filtered nitrogen, filtered $CO_2$ or similar non-reactive gasses to remove most of the remaining fluid clinging to the processed endosperm. The next process step is flushing the remaining endosperm with water of high quality. A water extraction fluid is circulated several times through the endosperm to remove the remaining dextrins, oligosaccharides and sugars. A second gas "blow down" with filtered air, filtered nitrogen, filtered $CO_2$ or similar non-reactive gas then occurs. A second purified water flush is usually necessary to fully remove the remaining dextrins, oligosaccharides and sugars. The second water flush is followed by a third gas "blow down" with filtered air, filtered nitrogen, filtered $CO_2$ or similar non reactive gas, to remove most of the remaining fluid clinging to the processed endosperm.

The total volume of the flush extraction liquid is calculated to match the volume of extraction fluid water necessary to process a second batch of endosperm to the required sugar concentration for fermentation. The flush fluids are stored for use as extraction fluid for subsequent batches of endosperm and, hence, no sugars and residual enzymes are lost from the total operation.

The next operation on the remaining endosperm extracts zein proteins from the remaining endosperm. The zein proteins are extracted by circulating a 70% (v/v) ethanol-water mixture at a temperature of 50° F. to 160° F. (optimum at 70° F.). Dehydrated ethanol from the fuel ethanol process is fed into the system, depending on the moisture level of the residual endosperm. The temperature is adjusted to the process temperature by the circulation heat exchanger. The fluid circulates for a period of 0.5 to 5 hours (optimum of 1 hr) until the zein protein dissolves in the ethanol fluid.

At the end of the zein protein extraction process, the process fluid is pumped out of the system. The endosperm containment vessel and total circulation system then receives a gas "blow down" with filtered air, filtered nitrogen, filtered $CO_2$, or similar non reactive gasses, to remove most of the remaining fluid clinging to the processed endosperm. The "blow down" is followed by a flush with purified water, one-tenth to two tenths of the process volume, to flush the system of any remaining ethanol liquid or vapor. The zein protein containing fluids are further processed externally to concentrate and/or precipitate the zein protein in the extraction fluid. The ethanol and water in the process fluid is then flashed to purify the ethanol water solution and then dehydrated in the fuel ethanol distillation and drying process.

The third and final process on the remaining endosperm in this example is digestion of the remaining unrecovered zein protein and other proteins, as well as remaining endosperm carbohydrate and other materials. At least 40% to 70% of the zein proteins are removed in the aqueous alcohol extraction process, and the remaining endosperm is 5% to 8% of its starting dry weight. This remaining material is digested primarily to liquefy it, and also to convert the remaining proteins to nitrogen compounds, easily incorporated as nutrients in the ethanol fermentation process.

A process fluid of 1% to 5% sulfuric, nitric acid, or similar strong acid solution, is circulated through the remaining endosperm in the containment vessel. The digestion temperature is between 190° F. to 250° F. at a pressure of between 0.6 atmospheres to 2.0 atmospheres. The temperature and resulting pressures are controlled by the recirculation heat exchanger and pressure controls on the containment vessel. The process time is between 0.5 and 4.0 hours for the digestion processes.

After digestion, the temperature and pressure of the system are adjusted to lower the temperature to the range of 70° F. to 120° F. for convenient handling and storage. The remaining liquefied endosperm is then removed from the system and transferred to storage for the fermentation process. Finally, the system is flushed with high purity water at 5% of the system volume to purge and clean the system for subsequent use.

While the invention has been particularly shown and described with reference to preferred embodiments thereof, it will be understood by those skilled in the art that various changes in form and details may be made therein without departing from the spirit and scope of the invention.

We claim:

1. A process for containment and product extraction of grain endosperm comprising the steps;
    (a) providing a system including a vessel having a contained volume therein for retaining grain endosperm and allowing passage of extraction fluids through the contained volume;
    (b) depositing grain endosperm within the contained volume;
    (c) passing a plurality of extraction fluids sequentially through the grain endosperm within the contained volume to extract selected components therefrom and sequentially remove each extraction fluid with selected components therein from the system; and
    (d) removing grain endosperm residual, if any, from the contained volume and from the system.

2. The process for containment and product extraction of grain endosperm of claim 1, wherein the grain endosperm is ground to a selected particle size range before depositing the endosperm within the contained volume.

3. The process for containment and product extraction of grain endosperm of claim 1, wherein the contained volume within the vessel is selected from the group consisting of a continuous screen barrier within the vessel, a pair of spaced, continuous screen barriers within the vessel and a cylindrical screen barrel suspended within the vessel.

4. The process for containment and product extraction of grain endosperm of claim 1, wherein the step of providing a system including a vessel having a contained volume therein retaining the grain endosperm includes providing a system including at least two vessels operated in parallel, each vessel having a contained volume therein retaining the grain endosperm, each vessel allowing passage of fluids through the contained volume.

5. The process for containment and product extraction of grain endosperm of claim 1, wherein step (c) comprises;
    (1) passing a first aqueous liquid phase containing enzymes through the grain endosperm within the contained volume at a selected temperature, pressure and pH for a time sufficient to produce dextrins, oligosaccharides, and sugars soluble in the aqueous liquid phase, and removing the first aqueous liquid phase from the system;
    (2) passing a first gas phase, then a second aqueous liquid phase, then a second gas phase through the contained volume to remove residual first aqueous liquid phase from the grain endosperm and from the system;
    (3) passing an aqueous alcohol liquid phase through the grain endosperm within the contained volume at a selected temperature, pressure and pH to extract zein proteins there from, and removing the aqueous alcohol liquid phase containing the zein proteins from the system;
    (4) passing a third gas phase, then a third aqueous liquid phase through the contained volume to remove residual aqueous alcohol liquid phase from the grain endosperm and from the system; and
    (5) passing a fourth aqueous liquid phase containing a strong acid through the grain endosperm within the contained volume at a selected temperature and pressure for a time sufficient to dissolve remaining grain endosperm and produce nutrient material soluble therein, and removing the fourth aqueous liquid phase containing the nutrient material from the system.

6. A process for containment and product extraction of grain endosperm comprising the steps:
    (a) providing a system including a vessel having a contained volume therein for retaining a ground grain endosperm and allowing passage of fluids through the contained volume;
    (b) depositing a ground grain endosperm having particles sized between 0.5 mm and 20 mm within the contained volume;
    (c) passing a first aqueous liquid phase containing enzymes through the ground grain endosperm within the contained volume at a selected temperature, pressure and pH for a time sufficient to produce dextrins, oligosaccharides, and sugars soluble in the aqueous liquid phase, then removing the first aqueous liquid phase from the system;
    (d) passing first a gas, then a second aqueous liquid phase, then another gas through the contained volume to remove residual first aqueous liquid phase from the ground grain endosperm and from the system;
    (e) passing an aqueous alcohol liquid phase through the ground grain endosperm within the contained volume at a selected temperature, pressure and pH to extract zein proteins therefrom, then removing the aqueous alcohol liquid phase containing the zein proteins from the system;
    (f) passing first a gas, then a third aqueous liquid phase through the contained volume to remove residual aqueous alcohol liquid phase from the ground grain endosperm and from the system; and
    (g) passing a fourth aqueous liquid phase containing a strong acid through the ground grain endosperm within the contained volume at a selected temperature and pressure for a time sufficient to dissolve remaining ground grain endosperm and produce nutrient material soluble in the fourth aqueous liquid phase, then removing the fourth aqueous liquid phase containing the nutrient material from the system.

7. The process for containment and product extraction of grain endosperm of claim 6, further comprising the step;
    (h) passing a fifth aqueous liquid phase through the contained volume and through the system to remove residue therefrom.

8. The process for containment and product extraction of grain endosperm of claim 6, further comprising after step (c), the step:
- ($c_2$) passing the first aqueous liquid phase containing enzymes, dextrins, oligosaccharides, and sugars to an ultrafiltration system, thereby producing a permeate aqueous liquid phase containing dextrins, oligosaccharides, and sugars retained for further processing and a concentrated retentate first aqueous liquid phase recycled to the first aqueous liquid phase passing through the ground grain endosperm of step (c).

9. The process for containment and product extraction of grain endosperm of claim 6, further comprising after step (c), the step:
- ($c_3$) passing the first aqueous liquid phase containing enzymes, dextrins, oligosaccharides, and sugars to a nanofiltration system, thereby producing a permeate aqueous liquid phase containing essentially sugars retained for further processing and a concentrated retentate first aqueous liquid phase recycled to the first aqueous liquid phase passing through the ground grain endosperm of step (c).

10. The process for containment and product extraction of grain endosperm of claim 6, further comprising after step (c), the steps:
- ($c_4$) passing the first aqueous liquid phase containing enzymes, dextrins, cyclodextrins, oligosaccharides, and sugars to a microfiltration/ultrafiltration system, thereby producing a concentrated retentate first aqueous liquid phase recycled to the first aqueous liquid phase passing through the ground grain endosperm of step (c), and a permeate liquid phase containing dextrins, cyclodextrins, oligosaccharides, and sugars;
- ($c_5$) passing the permeate liquid phase of step ($c_4$) through an ultrafiltration system, thereby producing a second retentate liquid phase containing cyclodextrins retained for further processing, and a second permeate liquid phase containing dextrins, oligosaccharides, and sugars; and
- ($c_6$) passing the second permeate liquid phase of step ($c_5$) through an nanofiltration system, thereby producing a third retentate concentrate liquid phase containing dextrins, oligosaccharides, and sugars retained for further processing, and a third dilute, permeate liquid phase recycled to the first aqueous liquid phase passing through the ground grain endosperm of step (c).

11. The process for containment and product extraction of grain endosperm of claim 6, wherein steps (d) and (f) are repeated at least a second time to remove additional aqueous phases from the ground grain endosperm.

12. The process for containment and product extraction of grain endosperm of claim 10, wherein all second aqueous liquid phases of steps (d) removed from the system are combined, additional enzymes added, and the combined aqueous liquid phase used as the first aqueous liquid phase in step (c) of the containment and product extraction process.

13. The process for containment and product extraction of grain endosperm of claim 6, wherein the contained volume within the vessel is selected from the group consisting of a continuous screen barrier within the vessel, a pair of spaced, continuous screen barriers within the vessel and a cylindrical screen barrel suspended within the vessel.

14. The process for containment and product extraction of grain endosperm of claim 6, wherein the step of providing a system including a vessel having a contained volume therein retaining the ground grain endosperm includes providing a system including at least two vessels operated in parallel, thereby enabling performance of nonidentical process steps in a single time period, each vessel having a contained volume therein retaining the ground grain endosperm, each vessel allowing passage of fluids through the contained volume.

15. The process for containment and product extraction of grain endosperm of claim 6, wherein the first aqueous liquid phase contains enzymes selected from the group consisting of alpha-amylase enzyme, glucoamylase enzyme, cyclodextrin glycosyltransferase enzyme and combinations thereof.

16. The process for containment and product extraction of grain endosperm of claim 6, wherein the first aqueous liquid phase has pH in the range 2.5 to 6.5 and passes through the ground grain endosperm at a temperature in the range 80° F. to 230° F. for 0.5 to 8.0 hours.

17. The process for containment and product extraction of grain endosperm of claim 7, wherein the second, third and fifth aqueous liquid phases comprise purified water.

18. The process for containment and product extraction of grain endosperm of claim 6, wherein the aqueous alcohol phase of step (e) contains 70% volume to volume ethanol in water and passes through the ground grain endosperm at a temperature in the range 50° F. to 160° F. for 0.5 to 5.0 hours.

19. The process for containment and product extraction of grain endosperm of claim 6, wherein the aqueous alcohol phase of step (e) contains 70% volume to volume ethanol in water, plus a strong acid providing a pH of 1.0 to 2.0, plus 0.025% to 0.20% by weight of a reducing agent, said aqueous alcohol phase passing through the ground grain endosperm at a temperature in the range 140° F. to 175° F. for 20 to 40 minutes.

20. The process for containment and product extraction of grain endosperm of claim 19, wherein the reducing agent is selected from the group consisting of sodium sulfite, sodium bisulfite and cysteine.

21. The process for containment and product extraction of grain endosperm of claim 6, wherein the fourth aqueous liquid phase contains 1% to 5% strong acid and passes through the ground grain endosperm at a temperature in the range 190° F. to 250° F. for 0.5 to 4.0 hours at a pressure in the range 0.6 to 2.0 atmospheres.

22. A process for containment and product extraction of grain endosperm comprising the steps:
- (a) providing a ground grain endosperm having particles sized between 0.5 mm and 20 mm;
- (b) providing a system including a vessel having a contained volume therein retaining the ground grain endosperm and allowing passage of fluids through the contained volume;
- (c) depositing the ground grain endosperm within the contained volume;
- (d) passing a first aqueous liquid phase containing enzymes through the ground grain endosperm within the contained volume at a selected temperature, pressure and pH for a time sufficient to produce dextrins, oligosaccharides, and sugars soluble in the aqueous liquid phase;
- (e) removing the first aqueous liquid phase from the system;
- (f) passing a gas through the ground grain endosperm within the contained volume to remove residual first aqueous liquid phase from the ground grain endosperm and from the system;
- (g) passing a second aqueous liquid phase through the ground grain endosperm within the contained volume to remove additional residual first aqueous liquid phase from the ground grain endosperm and from the system;
- (h) passing a gas through the ground grain endosperm within the contained volume to remove residual first and second aqueous liquid phases from the ground grain endosperm and from the system;
(i) passing an aqueous alcohol liquid phase through the ground grain endosperm within the contained volume at a selected temperature, pressure and pH to extract zein proteins therefrom;
(j) removing the aqueous alcohol liquid phase containing the zein proteins from the system;
(k) passing a gas through the ground grain endosperm within the contained volume to remove residual aqueous alcohol liquid phase from the ground grain endosperm and from the system;
(l) passing a third aqueous liquid phase through the ground grain endosperm to remove residual aqueous alcohol liquid phase from the ground grain endosperm and from the system;
(m) passing a fourth aqueous liquid phase containing a strong acid through the ground grain endosperm within the contained volume at a selected temperature and pressure for a time sufficient to dissolve remaining ground grain endosperm and produce nutrient material soluble in the fourth aqueous liquid phase;
(n) removing the fourth aqueous liquid phase containing the nutrient material from the system; and
(o) passing a fifth aqueous liquid phase through the contained volume and through the system to remove endosperm residue therefrom.

* * * * *